US00PP34088P2

(12) United States Plant Patent
Diessenbacher

(10) Patent No.: US PP34,088 P2
(45) Date of Patent: Apr. 5, 2022

(54) ***PAULOWNIA* TREE NAMED 'WEGROW-B6'**

(50) Latin Name: ***Paulownia* hybrid**
Varietal Denomination: WEGROW-B6

(71) Applicant: WeGrow GmbH, Tonisvorst (DE)

(72) Inventor: Peter Diessenbacher, Tonisvorst (DE)

(73) Assignee: WeGrow GmbH, Tonisvorst (DE)

( * ) Notice: Subject to any disclaimer, the term of this patent is extended or adjusted under 35 U.S.C. 154(b) by 0 days.

(21) Appl. No.: 17/300,258

(22) Filed: May 3, 2021

(51) Int. Cl.
*A01H 5/04* (2018.01)
*A01H 6/00* (2018.01)

(52) U.S. Cl.
USPC ..... Plt./216
CPC ..... *A01H 6/00* (2018.05)

(58) Field of Classification Search
USPC ..... Plt./216
CPC ..... A01H 6/00
See application file for complete search history.

*Primary Examiner* — Anne Marie Grunberg
(74) *Attorney, Agent, or Firm* — Samuel R. McCoy, Jr.

(57) ABSTRACT

A new and distinct *Paulownia* hybrid tree named 'WEGROW-B6' which is characterized by an upright trunk, fast vertical rate of growth, high frost resistance, and earlier flowering, and the stability of these characteristics from generation to generation.

5 Drawing Sheets

Latin name of the genus and species: The Latin name of the genus and species of the novel variety disclosed herein is *Paulownia* hybrid.

Variety denomination: The inventive variety of *Paulownia* hybrid disclosed herein has been given the variety denomination 'WEGROW-B6'.

BACKGROUND OF THE INVENTION

Parentage: The claimed tree is a seedling selection resulting from the controlled crosspollination of an unnamed *Paulownia elongata* S.Y. Hu tree (not patented), the seed parent, with an unnamed *Paulownia fortunei* Hemsl. tree (not patented), the pollen parent, at a tree plantation established at the experimental field of the University of Bonn in Rheinbach, Germany. In summer of 2014, after one year of cultivation, one tree growing amongst a population of 60 trees originating from the crossing in 2010 was observed to exhibit a faster rate of growth, early flowering initiation, and improved frost tolerance relative to other progeny and the parent plants. The tree was isolated for further evaluation in order to confirm the distinctness and stability of the characteristics first observed. In the summer of 2017, upon confirmation of distinctness and stability, 'WEGROW-B6' was selected for commercialization.

Asexual Reproduction: In the summer of 2016, 'WEGROW-B6' was first asexually reproduced by way of meristematic tissue culture micropropagation in Tönisvorst, Germany. The claimed tree was found to asexually reproduce in a uniform and stable manner and successive cycles of vegetative propagation have proven to be true to type.

SUMMARY OF THE INVENTION

The cultivar 'WEGROW-B6' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'WEGROW-B6'. These characteristics in combination distinguish 'WEGROW-B6' as a new and distinct *Paulownia* tree:

1. 'WEGROW-B6' exhibits a fast rate of growth with an upright trunk that rapidly increases in diameter and height which, when cultivated for timber production, equates to greater productivity; and
2. 'WEGROW-B6' exhibits a high degree of frost tolerance and cold hardiness to minus twenty-two degrees Celsius; and
3. 'WEGROW-B6' exhibits a strong homogenous stem development; and
4. 'WEGROW-B6' exhibits early flower initiation, with flower bud development beginning in late September and flowers opening in late March of the following year in Rheinbach, Germany.

BOTANICAL DESCRIPTION OF THE PLANT

Figure 1:
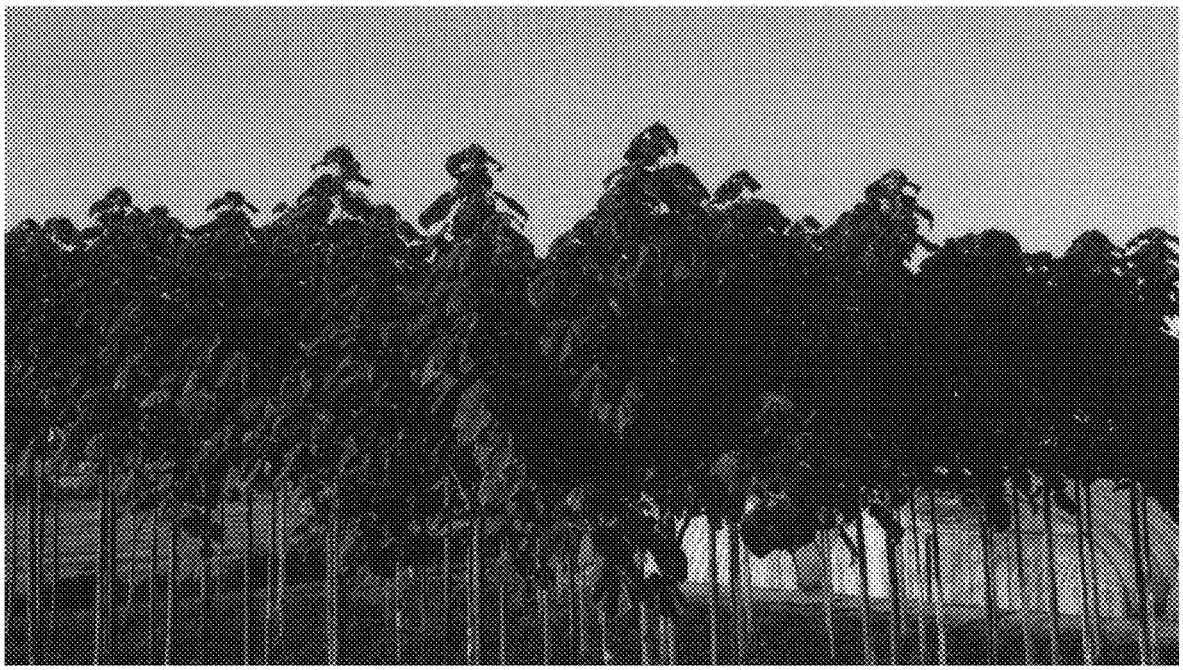
FIG. 1 illustrates, as nearly true as it is reasonably possible to make the same in color photographs of this type, a field-grown 'WEGROW-B6' tree at approximately 3.5 years of age, during spring in Tönisvorst, Germany.
Figure 2:
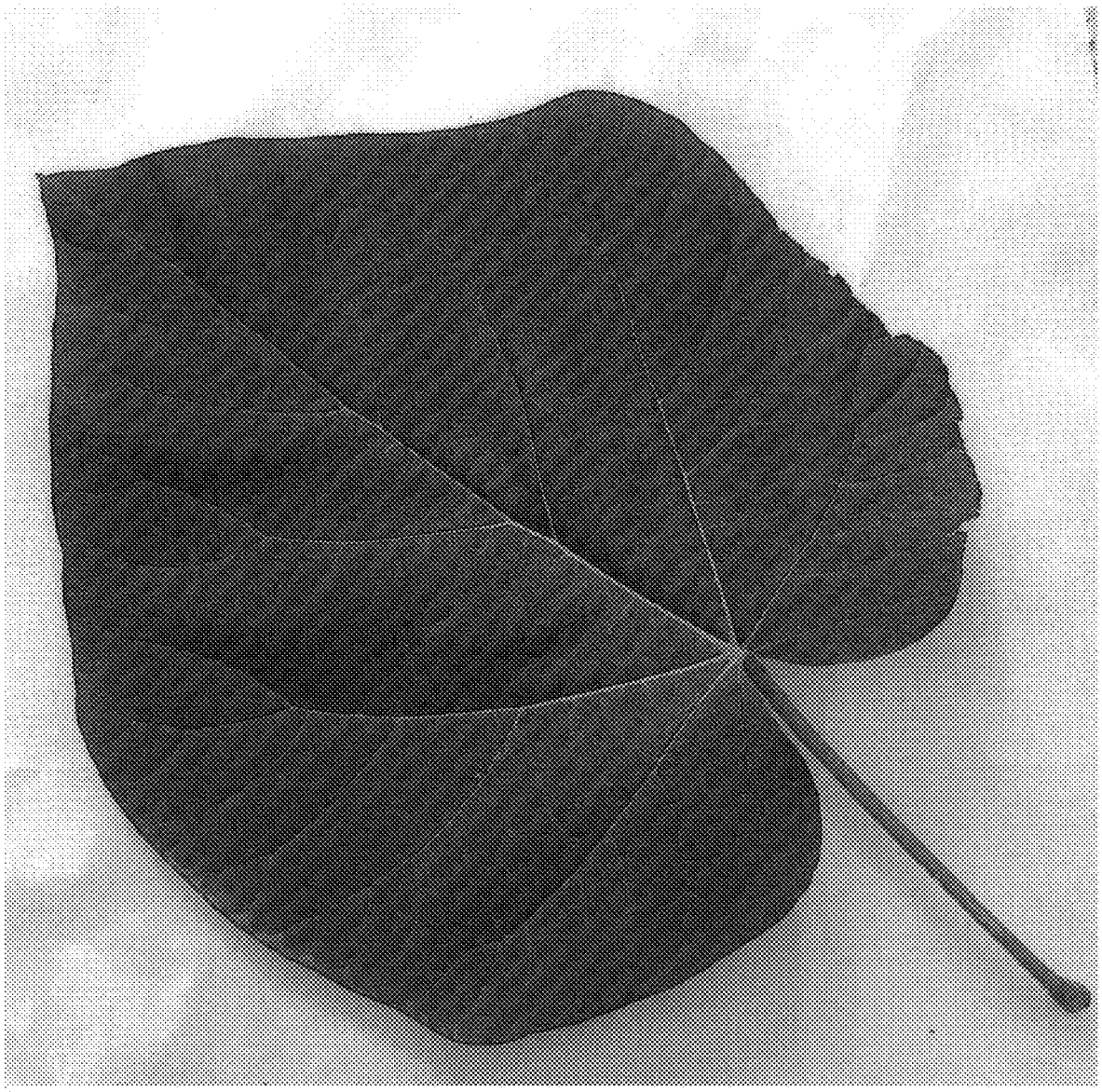
FIG. 2 illustrates, as nearly true as it is reasonably possible to make the same in color photographs of this type, the exemplary mature foliage of 'WEGROW-B6'.
Figure 3:
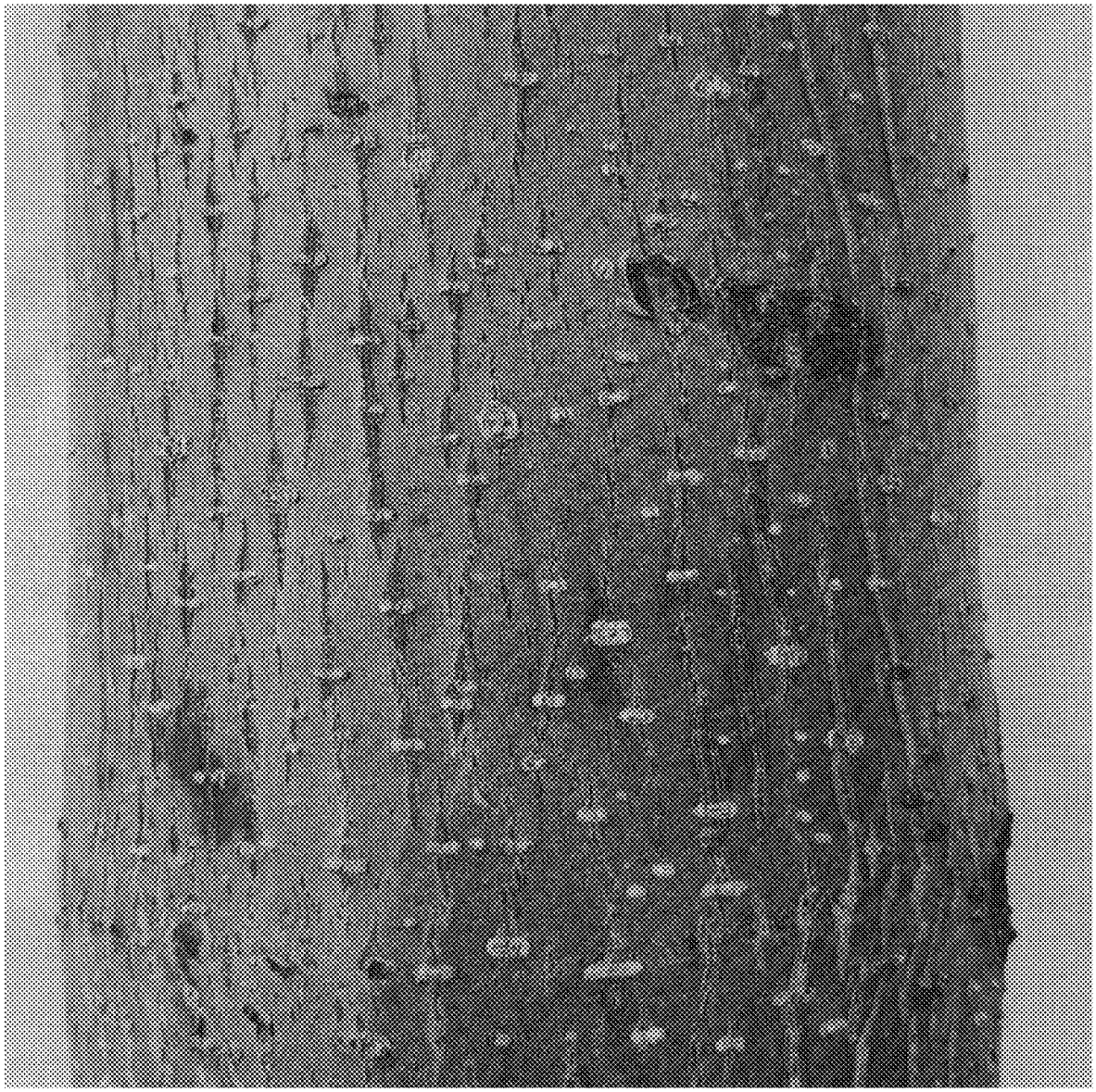
FIG. 3 illustrates, as nearly true as it is reasonably possible to make the same in color photographs of this type, the oldest wood of a mature field-grown 'WEGROW-B6' tree.
Figure 4:
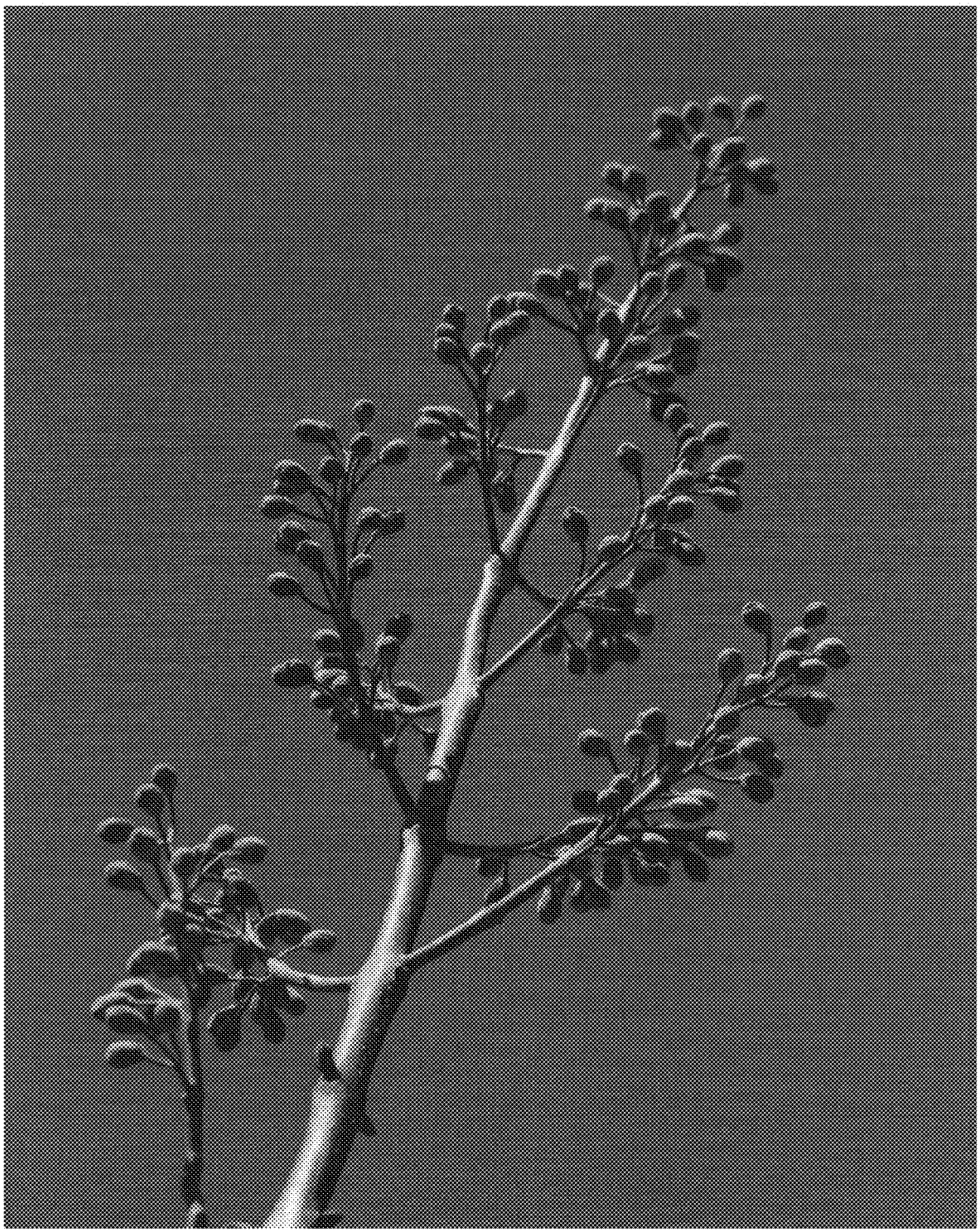
FIG. 4 illustrates, as nearly true as it is reasonably possible to make the same in color photographs of this type, the typical inflorescence of 'WEGROW-B6'.
Figure 5:
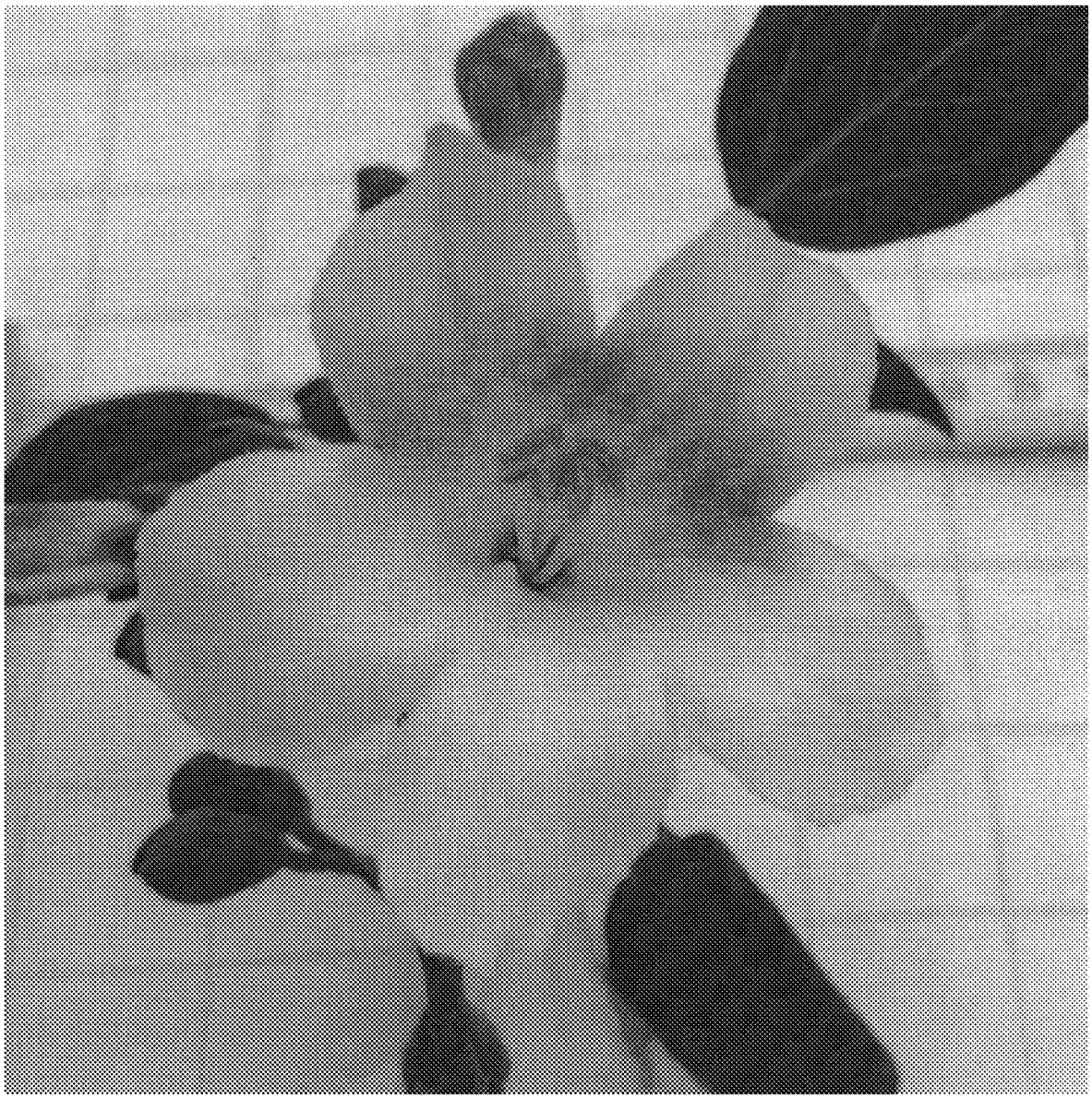
FIG. 5 illustrates, as nearly true as it is reasonably possible to make the same in color photographs of this type, the typical flowers of 'WEGROW-B6'.

The following is a detailed botanical description of a new and distinct *Paulownia* hybrid plant known as 'WEGROW- B6'. Plant observations were made on a 3.5 year-old field-grown tree in Tönisvorst, Germany. The observed tree was grown in full exposure to natural sunlight, and maintained with drip irrigation. No pest or pathogen countermeasures were employed. Two years after planting the observed tree into the field, the tree was pruned to the soil level in May of 2019 and allowed to regrow for approximately 1 year. Observation data was then recorded in March of 2020.

Those skilled in the art will appreciate that certain characteristics will vary with older or, conversely, younger plants. 'WEGROW-B6' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2015 (sixth edition).

A botanical description of 'WEGROW-B6' and comparisons with the parents and most similar commercial cultivar are provided below.

General plant description:

*Plant habit*.—Deciduous tree with an upright ascending, moderately-branching growth habit.

*Tree crown profile*.—Broad-ovate.

*Dimensions*.—The original tree grew to approximately 7.23 meters tall and 0.40 meters wide at 7 years of age.

*Plant vigor*.—Vigorous.

*Growth rate*.—Fast growing.

*Environmental tolerances*.—Cold hardy to at least minus 22 degrees Celsius; prefers well drained soils with regular irrigation, and full sun exposure.

*Pest and disease susceptibility or resistance*.—Plants have not been observed to be susceptible or resistant to pathogens and pests common to *Paulownia* sp.

*Propagation*.—Propagation is accomplished by way of meristematic tissue culture micropropagation.

*Crop time*.—When cultivated for timber production, approximately eight growing seasons are needed to first harvest and an additional two seasons for main harvest.

Root system:

*Description*.—A network of fibrous, non-fleshy roots.

*Rooting habit*.—Freely branching, moderately dense, and moderately deep in the soil profile; 4.5 to 9.0 meters deep.

Stems:

*Branching habit*.—A dominant, near-vertical central main stem, typically branched, gives rise to a strong formation of lateral branches.

*Main stem; dominant central leader*.—Quantity — One. Attitude — Erect; near vertical. Aspect — Generally rounded-ovate. Diameter — 40 cm, at breast height, on an 8 year-old tree. Strength — Very strong. Texture — Glabrous, lenticellate and becoming progressively fissured with age. Lenticels are irregularly elliptical to elliptical and range in size from 0.5 mm to 5.0 mm long and 1.0 to 5.0 mm wide. Color is greyed-green, nearest to in between RHS 195A and 199D. Color, juvenile — Greyed-Brown, nearest to a mixture of RHS 195D, 199B, 197C, and 200A; irregularly blotched and banded with greyed-green, nearest to RHS 195A. Moderately suffused with a mixture of green, RHS 144A, and yellow-green, RHS 146A; suffusion becomes less pronounced as the wood ages. Color, oldest wood — Brown, nearest to a mixture of RHS 195B, 195D, 197A, 200A, 200B, 200C and 200D; irregularly blotched and banded with greyed-green, nearest to RHS 194B; fissures are nearest to in between yellow-green and greyed-orange; RHS 197A, 152A and 177B.

*Lateral branches*.—Quantity primary lateral branch es — 5 to 7, on average. Quantity of secondary lateral branches — 14.6, on average. Attitude — Slightly oblique, right-angle branches, relative to the main stem. Aspect — Wide-ovate. Diameter at breast height — 10.40 cm, on average. Diameter at the root collar — 14.48 cm, on average. Stem strength — Strong. Texture and luster — Glabrous, moderately glossy, and moderately lenticellate. Lenticels are irregularly elliptical to elliptical and range in size from 1.0 mm to 5.0 mm long and 1.0 to 4.0 mm wide; color is greyed-green, nearest to in between RHS 193C and 195D. Color — Greyed-green, nearest to a mixture of RHS 194C, 195A, and 197B; irregularly blotched and banded with greyed-green, nearest to RHS 146D. Moderately suffused with a mixture of green, RHS 144A, and yellow-green, RHS 145C.

Foliage:

*Arrangement*.—Opposite.

*Attachment*.—Petiolate.

*Division*.—Simple.

*Shape*.—Wide-ovate to cordate.

*Length*.—41.6 cm, on average.

*Width*.—37.06 cm, on average.

*Apex*.—Cuspidate.

*Base*.—Cordate.

*Margin*.—Ciliate; and serrate to doubly serrate in young plants; slightly to moderately undulated.

*Aspect*.—Flat.

*Texture and pubescence, adaxial surface*.—Glabrous, slightly bullate, and slightly glossy.

*Texture and pubescence, abaxial surface*.—Pubescent, slightly bullate and matte.

*Color*.—Juvenile foliage, adaxial surface — Yellow-green, nearest to in between RHS N140D and N141C, and suffused light blue, RHS 106D. Juvenile foliage, abaxial surface — Yellow-green, nearest to in between RHS 143B and 143D. Mature foliage, adaxial surface — Yellow-green, nearest to a mixture of RHS N144A, N144B and N144C. Mature foliage, abaxial surface — Yellow-green, nearest to in between RHS 144C and N144B.

*Venation*.—Pattern — Reticulate. Vein color, adaxial surface — Yellow-green, nearest to RHS 142D and 144D. Vein color, abaxial surface — Yellow-green, nearest to in between RHS N144B and N144D.

*Petiole*.—Length — Ranging from 10.0 to 14.0 mm. Diameter — Ranging from 0.6 to 1.0 cm. Texture, adaxial and abaxial surfaces — Moderately pubescent. Color, adaxial and abaxial surfaces — Yellow-green, nearest to a mixture of RHS 145B and N144A, and suffused with yellow-green, RHS 144D. Trichomes — Present on the abaxial surface; mostly glandular but occasionally dendroid.

Inflorescence:

*Habit*.—Large terminal thyrses; pyramidal in profile.

*Natural flowering season*.—Buds develop in late September and into early October, Rheinbach, Germany, and remain unopened through winter; flowers then emerge in the following spring, in late March.

*Attitude*.—Erect.

*Inflorescence dimensions*.—Typically ranging from 16 to 25 cm long and 14 to 20 cm wide.

*Quantity of flowers per inflorescence*.—Approximately 20 flowers and buds, with 3 to 4 flowers and buds per peduncular branch of the inflorescence.

*Peduncle*.—Color — A mixture of RHS 170A, 170B, 171A, and 172C. Texture — Totnentose. Strength — Strong.

Flower bud:

*Shape*.—Ovoid.

*Dimensions*.—1.75 cm long and 1.0 cm wide, prior to bud break.

*Texture*.—Tomentose.

*Bud color*.—Nearest to a mixture of RHS N167A, N170A, 170B, 171A, and 172C.

Flower:

*Type and shape*.—Zygomorphic; funnelform; proximal portion of the petals are fused with five free petal lobes, distally.

*Dimensions*.—8 cm long and 4 cm wide.

*Attitude*.—Upward and outward.

*Persistence*.—Flowers persist for approximately one month.

*Fragrance*.—Mild vanilla, creamy-spice fragrance; fragrance is stronger at night.

*Pedicels*.—Dimensions — 2.0 to 2.5 cm long and 0.8 to 1.4 cm in diameter. Color — A mixture of RHS 170A, 170B, 171A, and 172C. Texture — Tomentose. Strength — Strong.

*Calyx*.—Calyx shape — Shallowly campanulate; sepals fused, proximally. Dimensions — 2.8 to 3.0 cm long and 1.9 to 2.3 cm wide. Sepal lobes — Quantity of sepal lobes — Four. Dimensions — 2.2 to 3.0 cm long and 0.5 to 0.8 cm wide at the base. Shape — Ovate. Sepal apex — Acute. Sepal base — Fused. Sepal margin — Entire. Sepal texture — Tomentose; densely covered with a hairy indumentum. Sepal color, inner surface — A mixture of RHS 166B, 166C, N167A, and N167B. Sepal color, outer surface — A mixture of RHS 166B, 166C, N167A, N167B.

*Corolla*.—Petal lobes — Quantity — Five. Shape of petal lobes — Rounded. Dimensions of the lobes — 2.5 cm long and 2.5 cm wide. Apex — Obtuse. Base — Fused at the base. Margin — Ciliate; moderately undulated. Aspect — Moderately reflexed. Texture, inner surface — Glabrous. Texture, outer surface — Glabrous. Color, inner surface — White, nearest to RHS NN155D; when viewed in a vertical plane, the upper portion of the corolla is moderately to heavily suffused with violet, RHS 92C, while the lower portion of the corolla is very lightly suffused with violet, RHS 92D. Striped with light yellow at the points of fusion of the lowermost petal lobes, RHS 8C, when viewed in a vertical plane. Color, outer surface — White, RHS NN155D, and very lightly suffused with yellow, nearest to RHS 2D; when viewed in a vertical plane, the upper portion of the corolla is moderately to heavily suffused with violet, RHS 91C while the lower portion of the corolla is very lightly suffused with violet, RHS 92D. Striped with light yellow at the points of fusion of the lowermost petal lobes, RHS 2C, when viewed in a vertical plane.

Reproductive organs:

*Androecium*.—Stamens — Four didynamous stamens, with filaments fused to the floral tube; twisted near the base; sparsely glandular to hairy. Stamen length — 4.0 to 5.5. cm long, with two stamens being longer than the others. Filament — Length — 3.5 to 4.5 cm long. Color — Nearest to a mixture of RHS NN155A, 155D, and 157A. Anther — Shape — Divergent; narrow. Dimensions — 6 to 10 mm long and 0.3 to 0.4 cm wide. Color — Nearest to a mixture of RHS NN155A, 155C, 155D, 156A, and 157A. Pollen — Shape — Round to triangular; convex; spheroid; reticulate. Dimensions — 21 μm. Pollen color — Nearest to in between 2D and 4D.

*Gynoecium*.—Pistil quantity — One. Pistil length — 6.5 to 7.5 cm long. Stigma — General description — The slightly bilobate stigma tip has a single small hole that leads to a tubular dilated chamber at the top of the style covered in receptive papillae. Diameter — 2.0 to 2.3 mm. Color — Nearest to a mixture of RHS NN155A, 155C, 155D, 156A, and 157A. Style — Length — 5.5 to 6.5 cm. Color — Nearest to a mixture of RHS NN155A, 155C, 155D, 156A, and 157A. Ovary — General description — Bilocular. Dimensions — 2.4 cm long and 1.0 cm wide.

Fruit and seed:

*Fruit*.—General — The ovary develops into a sticky oval capsule tapered at the apex with the remaining desiccated style sometimes still attached. The capsule remains on the persistent calyx, where they can last on the tree through the rest of the year before turning woody and loculicidal dehiscence. Shape — Oblong; elliptical. Dimensions — 4.5 to 5.5 cm long and 9.0 to 1.01 cm wide. Texture — Tomentose. Color — Nearest to a mixture of RHS 152C, 152B, 153B, 144B, 163A, and 167A; pubescence is RHS 145D.

*Seed*.—General — The membranous and winged seeds are very light and soft; wings gradually increase in length around the seed. The ventral and dorsal sides of the seed are flat. Dimension — 2 to 7 mm long and 20 to 23 mm wide. Color — Nearest to a mixture of RHS NN155D, 8D, and 150D. Maturity time — Autumn.

COMPARISON WITH THE PARENT PLANTS

Plants of the new cultivar 'WEGROW-B6' differ from the seed parent, an unnamed *Paulownia elongata* tree (not patented), by the following characteristics described in Table 1.

TABLE 1

| Characteristic | 'WEGROW-B6' | The seed parent |
|---|---|---|
| Growth rate of stem diameter. | Slow. | Intermediate. |
| Vertical growth rate. | Fast. | Intermediate. |
| Attitude of the dominant central leader. | Erect. | Curved. |

Plants of the new cultivar 'WEGROW-B6' differ from the pollen parent, an unnamed *Paulownia fortunei* tree (not patented), by the following characteristics described in Table 2.

TABLE 2

| Characteristic | 'WEGROW-B6' | The pollen parent |
|---|---|---|
| Tree height | Significantly shorter than the pollen parent. | Significantly taller than 'WEGROW-B6'. |
| Cold hardiness. | Significantly more cold hardy than the pollen parent. | Much less cold hardy than 'WEGROW-B6'. |
| Vertical growth. | Faster than the pollen parent. | Slower than 'WEGROW-B6'. |

COMPARISON WITH THE MOST SIMILAR *PAULOWNIA* HYBRID CULTIVAR KNOWN TO THE INVENTOR

Plants of the new cultivar 'WEGROW-B6' differ from the closest known commercial comparator, *Paulownia* 'Phoenix One' (Community Plant Variety Rights Grant number EU 39980), in the following Characteristics described in Table 3.

TABLE 3

| Characteristic | 'WEGROW-B6' | 'Phoenix One' |
|---|---|---|
| Main stem girth; rate of growth. | Slower than the 'Phoenix One'. | Faster than 'WEGROW-B6'. |
| Main stem; rate of vertical growth. | Faster than the 'Phoenix One'. | Slower than 'WEGROW-B6'. |
| Time to flower. | Early flower initiation; bud development is initiated in late September with flowers opening in late March of the following year. | Does not flower in European climates. |
| Cold hardiness. | More cold hardy; to minus-22 degrees Celsius. | Less hardy; to minus-10 degrees Celsius. |

That which is claimed is:

1. A new and distinct variety of *Paulownia* hybrid tree named 'WEGROW-B6', substantially as described and illustrated herein.

* * * * *